(12) United States Patent
Jørgensen et al.

(10) Patent No.: US 11,205,253 B2
(45) Date of Patent: Dec. 21, 2021

(54) ENHANCING THE VISIBILITY OF BLOOD VESSELS IN COLOUR IMAGES

(71) Applicant: AMBU A/S, Ballerup (DK)

(72) Inventors: Andreas Härstedt Jørgensen, Rødovre (DK); Finn Sonnenborg, Frederikssund (DK)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 17/273,116

(22) PCT Filed: Sep. 3, 2019

(86) PCT No.: PCT/EP2019/073483
§ 371 (c)(1),
(2) Date: Mar. 3, 2021

(87) PCT Pub. No.: WO2020/048997
PCT Pub. Date: Mar. 12, 2020

(65) Prior Publication Data
US 2021/0342985 A1   Nov. 4, 2021

(30) Foreign Application Priority Data
Sep. 7, 2018  (EP) .................................. 18193186

(51) Int. Cl.
*G06T 5/00*   (2006.01)
*A61B 5/00*   (2006.01)
(Continued)

(52) U.S. Cl.
CPC .......... *G06T 5/007* (2013.01); *A61B 1/00045* (2013.01); *A61B 1/04* (2013.01);
(Continued)

(58) Field of Classification Search
CPC . G06T 5/007; G06T 5/50; G06T 2207/10024; G06T 2207/30101; A61B 1/00045; A61B 1/04; A61B 5/489
See application file for complete search history.

(56) References Cited

U.S. PATENT DOCUMENTS

| 4,583,027 A | 4/1986 | Parker |
| 5,942,817 A | 8/1999 | Chitayat |

(Continued)

FOREIGN PATENT DOCUMENTS

| EP | 2474265 A2 | 7/2012 |
| EP | 3123927 A1 | 2/2017 |

(Continued)

OTHER PUBLICATIONS

Communication under Rule 71(3), Intention to Grant, issued in EP 18 193 186.6, dated May 27, 2021, 9 pages.
(Continued)

*Primary Examiner* — Brenda C Bernardi
(74) *Attorney, Agent, or Firm* — Faegre Drinker Biddle & Reath LLP (57) ABSTRACT

A method of enhancing the visibility of blood vessels in a colour image captured by an image capturing device of a medical device, the colour image having a plurality of colour channels and a plurality of pixels, the method including for at least some of said plurality of pixels the steps of: (a) processing data obtained from a first colour channel together with data obtained from a second colour channel to determine a value of a first parameter indicative of the intensity in the red spectrum relative to the total intensity of said pixel; and (b) using said value of said first parameter to alter said pixel, wherein said first parameter has at least three possible values, and wherein the strength of the alteration is dependent on the value of said first parameter.

34 Claims, 6 Drawing Sheets

(51) Int. Cl.
*G06T 5/50* (2006.01)
*A61B 1/00* (2006.01)
*A61B 1/04* (2006.01)

(52) U.S. Cl.
CPC .............. *A61B 5/489* (2013.01); *G06T 5/50* (2013.01); *G06T 2207/10024* (2013.01); *G06T 2207/30101* (2013.01)

(56) References Cited

U.S. PATENT DOCUMENTS

| | | | |
|---|---|---|---|
| 6,956,602 | B2 | 10/2005 | Higuchi et al. |
| 9,854,962 | B2 | 1/2018 | McGrail et al. |
| 10,321,804 | B2 | 6/2019 | Jacobsen et al. |
| 10,406,309 | B2 | 9/2019 | Daher |
| 10,478,054 | B2 | 11/2019 | Nave et al. |
| 2003/0071895 | A1 | 4/2003 | Higuchi et al. |
| 2012/0179050 | A1 | 7/2012 | Saito |
| 2014/0316283 | A1 | 10/2014 | Kaku et al. |
| 2016/0239965 | A1 | 8/2016 | Kuramoto |
| 2017/0014021 | A1 | 1/2017 | Kuramoto |
| 2017/0330320 | A1 | 11/2017 | Lynch et al. |
| 2018/0068437 | A1 | 3/2018 | Bronkalla et al. |
| 2018/0303351 | A1* | 10/2018 | Mestha ................ G06T 7/0016 |
| 2020/0211190 | A1 | 7/2020 | Jrgensen et al. |

FOREIGN PATENT DOCUMENTS

| | | |
|---|---|---|
| EP | 3127469 | 2/2017 |
| JP | 2016-174836 A | 10/2016 |
| JP | 2016174836 A * | 10/2016 |

OTHER PUBLICATIONS

Notice of allowance in CIP U.S. Appl. No. 16/811,927, dated Jun. 14, 2021, 5 pages.

Extended search report issued in EP 18 193 186.6, dated Nov. 19, 2020, 5 pages.

European search report issued in EP 18 193 186.6, dated Mar. 26, 2019, 6 pages.

Golhar, Mayank et al. "Blood Vessel Delineation in Endoscopic Images with Deep Learning Based Scene Classification," Intelligent Virtual Agent, Berlin, pp. 147-168, Jun. 16, 2018.

International Search Report and Written opinion in related International Application No. PCT/EP2019/073483, dated Nov. 28, 2019; 5 pages.

Search Report issued by the European Patent Office dated Nov. 19, 2020 in related European Application No. 18193186.6; 5 pages.

* cited by examiner

ENHANCING THE VISIBILITY OF BLOOD VESSELS IN COLOUR IMAGES

CROSS-REFERENCE TO RELATED APPLICATIONS

This application is a National Stage entry under 35 U.S.C. § 371 of International Application No. PCT/EP2019/073483, filed Sep. 3, 2019, which claims the benefit of and priority from European Application No. 18193186.6, filed Sep. 7, 2018.

FIELD

The present disclosure relates to a method of enhancing the visibility of blood vessels in colour images captured by an image capturing device of a medical device, an image processing device for enhancing the visibility of blood vessels in colour images, an image processing device for identifying potential pathological vascular structures, a display unit for displaying images obtained by an image capturing device, and an endoscope system.

BACKGROUND

Changes in the vascular structure of internal cavities may be indicative of a number of diseases such as autoimmune diseases and cancers. Typically, the vascular structures are examined using a medical device such as a standard endoscope or a camera pill (capsule endoscope). The medical device typically comprises a light source for illuminating the internal cavity and an image capturing device, i.e. camera for capturing images.

It may however be difficult for the medical personal to correctly and precisely analyse the vascular structures since the blood vessels may blend in with the surrounding tissue types. The visibility of the blood vessels may be improved by providing the medical device with an additional light source emitting light with a narrow wavelength that is selected so that blood vessels have a high absorption of the light relative to the surrounding tissue.

This will however increase the cost of the medical device and furthermore change the colours of the resulting image. The change in the colours may make it more difficult for the medical personal to navigate the medical device and furthermore examine changes in other tissue types of the internal cavities that may be indicative of a pathological condition.

U.S. Pat. No. 6,956,602 discloses an apparatus that includes a level adjusting circuit that increases a gain of a G (or B) signal output from a colour conversion circuit, a binarization circuit that forms a binarized image from this G signal and an edge detection circuit that extracts blood vessel position signals through edge detection based on this binarized signal. Then, the apparatus extracts RGB colour signals making up a blood vessel image by using the above-described blood vessel position signals, increases the gains of these blood vessel colour signals and then adds the blood vessel colour signals to the colour signals of an original image.

It may however be difficult to precisely determine the location of the blood vessels in the image. Thus areas of the image originating from blood vessels may not be enhanced whereas areas of the images not originating from blood vessels may be enhanced.

Thus it remains a problem to provide an improved method/device/system for enhancing the visibility of blood vessels in colour images recorded by an image capturing device of a medical device.

SUMMARY

According to a first aspect, the present disclosure relates to a method of enhancing the visibility of blood vessels in a colour image captured by an image capturing device of a medical device, said colour image having a plurality of colour channels and having a plurality of pixels, wherein said method comprises for at least some of said plurality of pixels the steps of:

(a) processing data obtained from a first colour channel together with data obtained from a second colour channel to determine a value of a first parameter indicative of the intensity in the red spectrum relative to the total intensity of said pixel;

(b) using said value of said first parameter to alter said pixel, wherein said first parameter has at least three possible values, and wherein the strength of the alteration is dependent on the value of said first parameter.

Consequently, by using information from at least two colour channels more information in the colour image may be used to estimate the location of the blood vessels allowing a more precise estimate. Furthermore, by using a non-binary value to determine the degree of alterations a more robust method is provided creating more lifelike images.

The medical device may be a medical device adapted to be introduced into a body cavity such as the body cavities of the digestive system or a body cavity of the airways. The medical device may be an elongated rigid or flexible endoscope, a capsule endoscope or laryngoscope. The medical device may comprise one or more light sources configured to emit substantially white light. The medical device may be a single use elongated flexible endoscope. The image capturing device may be arranged at a distal portion of an endoscope e.g. at the tip of an endoscope. The image capturing device may be operatively connectable to an image processing device configured to process the image data. Alternatively/additionally, the medical device may comprise an image processing device configured to process the image data. The colour images may be coded in any colour space such as an RGB type colour space or an YCbCr type colour space. The colour images may comprise at least three colour channels. The steps of the method e.g. step (a) and step (b) may be performed on the pixels of the colour images in parallel e.g. step (a) may be performed for all pixels in the image and then subsequently step (b) may be performed for all pixels in the image. Alternatively, the steps of the method may be performed sequential e.g. step (a) and step (b) may be performed on the pixels of the colour images sequential e.g. step (a) and (b) may be performed on a first pixel and then subsequent step (a) and (b) may be performed on a second pixel and so forth. Estimating a value of a first parameter indicative of the intensity in the red spectrum relative to the total intensity has shown to be a good indicator of blood vessels. The value may be a more precise indicator of the intensity in the red spectrum relative to the total intensity if information from all colour channels are used, however the value may also be determined using only information from only some colour channels e.g. two out of three colour channels.

In some embodiments, step (a) comprises: processing data obtained from a first colour channel together with data obtained from a second colour channel and data obtained from a third colour channel to determine a value of said first parameter.

Consequently, by using more data a more precise estimate of the location of the blood vessels may be provided.

In some embodiments, said data obtained from the first colour channel is processed together with said data obtained from the second colour channel to create a value of a first sub parameter, said data obtained from said first colour channel is processed together with said data obtained from said third colour channel to create a value of a second sub parameter, and wherein said value of said first sub parameter is processed together with said value of said second sub parameter to create said value of said first parameter.

In some embodiments, said value of said first parameter is created by calculating an average of said value of the first sub parameter and the value of the second sub parameter.

The average may be a weighted average or an unweighted average.

In some embodiments, step (a) comprises subtracting said data obtained from the second colour channel from said data obtained from the first colour channel.

As an example, if the first colour channel represents red and the second colour channel represents green then a large output will result when the red component of the pixel is significantly higher than the green component.

Consequently, a simple way of determining a value of a parameter indicative of the intensity in the red spectrum relative to the total intensity of the pixel is provided.

In some embodiments, the first parameter may have at least 8 possible values, 16 possible values or 32 possible values.

Consequently, the alteration of the image may be done effectively without introducing unnatural high frequency elements.

In some embodiments, both said value of said first sub parameter and said value of said second sub parameter are indicative of the intensity in the red spectrum relative to the total intensity of said pixel.

In some embodiments, said value of said first sub parameter is created by subtracting said data obtained from the second colour channel from said data obtained from the first colour channel, and wherein said value of said second sub parameter is created by subtracting said data obtained from the third colour channel from said data obtained from the first colour channel.

As an example, if the first colour channel represents red, the second colour channel represents green, and the third colour channel represents blue then the value of both the first sub parameter and the second sub parameter will be large when the red component of the pixel is significantly higher than both the green component and the blue component.

The value of the first parameter may also be determined by calculating a ratio between the data obtained from the first colour channel and the sum of the data obtained from the first colour channel, the second colour channel and/or the third colour channel e.g. by dividing the data obtained from the first colour channel with the sum of the data obtained from the first colour channel, the second colour channel and/or the third colour channel.

In some embodiments, parts of the colour image having no blood vessels are substantially unaltered and displayed with normal colours.

In some embodiments, step (b) comprises subtracting or adding a value of an alteration parameter from the value of at least one colour channel of the plurality of colour channels of said colour image, wherein the value of the alteration parameter is related to the value of the first parameter.

The value of the alteration parameter may simply be the value of the first parameter. The alteration parameter may be subtracted from all colour channels of said colour image.

In some embodiments, said method further comprises:
determining a value of a second parameter indicative of the intensity of said pixel and wherein said value of said first parameter together with said value of said second parameter is used to alter said pixel.

This may allow the method to decrease the strength of the alterations in dark areas of the colour image, where noise may make it difficult to precisely determine blood vessel locations.

In some embodiments, said plurality of colour channels are normalized prior to being processed together.

In some embodiments, a low pass filtered image is created for each of said plurality of colour channels indicating a local average for each pixel, and wherein each colour channel is normalized using its low pass filtered image.

In some embodiments, said colour image is an RGB colour image said first colour channel being the red colour channel and said second colour channel being the green or blue colour channel.

In some embodiments, said medical device is configured to be inserted into a body cavity and illuminate said body cavity with white light when said colour image is being recorded.

In some embodiments, a value of a third parameter is created based on user input, and wherein the alteration is dependent on both said value of said first parameter and said value of said third parameter, whereby the user may control the strength of the alteration.

As an example the value of an alteration parameter may be found by multiplying the value of the first parameter with the value of the third parameter and possibly also the value of the second parameter.

In some embodiments, said medical device is an endoscope.

In some embodiments, a high value of the first parameter indicates a high intensity in the red spectrum relative to the total intensity of said pixel and a low value of the first parameter indicates a low intensity in the red spectrum relative to the total intensity of said pixel.

In some embodiments, values of the first parameter that are among the 50% highest of all possible values results in alterations that are more significant than the alterations that results from values of the first parameter that are among the 50% lowest of all possible values.

In some embodiments, for at least 50% of the possible values of said first parameter an increase in the value of the first parameter results in an increase in the strength of the alteration.

In some embodiments, the alteration of said pixel is independent of the intensity in the green spectrum relative to the blue spectrum.

According to a second aspect, the present disclosure relates to an image processing device for enhancing the visibility of blood vessels in a colour image, said image processing device comprising a processing unit operationally connectable to an image capturing device of a medical device, wherein said processing unit is configured to receive a colour image having a plurality of colour channels from said image capturing device, said colour image has a plurality of pixels and wherein said processing unit further is configured to for at least some of said plurality of pixels perform the steps of:

(a) process data obtained from a first colour channel together with data obtained from a second colour channel to determine a value of a first parameter indicative of the intensity in the red spectrum relative to the total intensity of said pixel;

(b) using said value of said first parameter to alter said pixel, wherein said first parameter has at least three possible values, and wherein the strength of the alteration is dependent on the value of said first parameter.

In some embodiments, step (a) comprises: processing data obtained from a first colour channel together with data obtained from a second colour channel and data obtained from a third colour channel to determine a value of said first parameter.

In some embodiments, said data obtained from the first colour channel is processed together with said data obtained from the second colour channel to create a value of a first sub parameter, said data obtained from said first colour channel is processed together with said data obtained from said third colour channel to create a value of a second sub parameter, and wherein said value of said first sub parameter is processed together with said value of said second sub parameter to create said value of said first parameter.

In some embodiments, said value of said first parameter is created by calculating an average of said value of the first sub parameter and the value of the second sub parameter.

In some embodiments step (a) comprises subtracting said data obtained from the second colour channel from said data obtained from the first colour channel.

In some embodiments, the first parameter may have at least 8 possible values, 16 possible values or 32 possible values.

In some embodiments, both said value of said first sub parameter and said value of said second sub parameter are indicative of the intensity in the red spectrum relative to the total intensity of said pixel.

In some embodiments, said value of said first sub parameter is created by subtracting said data obtained from the second colour channel from said data obtained from the first colour channel, and wherein said value of said second sub parameter is created by subtracting said data obtained from the third colour channel from said data obtained from the first colour channel.

In some embodiments, parts of the colour image having no blood vessels are substantially unaltered and displayed with normal colours.

In some embodiments, step (b) comprises subtracting or adding a value of an alteration parameter from the value of at least one colour channel of the plurality of colour channels of said colour image, wherein the value of the alteration parameter is related to the value of the first parameter.

In some embodiments, said processing unit is further configured to: determine a value of a second parameter indicative of the intensity of said pixel and wherein said value of said first parameter together with said value of said second parameter are used to alter said pixel.

In some embodiments, said plurality of colour channels are normalized prior to being processed together.

In some embodiments, a low pass filtered image is created for each of said plurality of colour channels indicate a local average for each pixel, and wherein each colour channel is normalized using its low pass filtered image.

In some embodiments, said value of said first sub parameter is created by subtracting said data obtained from the second colour channel from said data obtained from the first colour channel, and wherein said value of said second sub parameter is created by subtracting said data obtained from the third colour channel from said data obtained from the first colour channel.

In some embodiments, said colour image is a RGB colour image said first colour channel being the red colour channel and said second colour channel being the green or blue colour channel.

In some embodiments, said medical device is configured to be inserted into a body cavity and illuminate said body cavity with white light when said colour images are being recorded.

In some embodiments, said image processing device is operationally connectable to an input unit for receiving user input and further configured to receive a user selected value of a third parameter from said input unit and wherein the alteration is dependent on both said value of said first parameter and said value of said third parameter, whereby the user may control the strength of the alteration.

In some embodiments, said medical device is an endoscope.

In some embodiments, a high value of the first parameter indicates a high intensity in the red spectrum relative to the total intensity of said pixel and a low value of the first parameter indicates a low intensity in the red spectrum relative to the total intensity of said pixel.

In some embodiments, values of the first parameter that are among the 50% highest of all possible values results in alterations that are more significant than the alterations that results from values of the first parameter that are among the 50% lowest of all possible values.

In some embodiments, for at least 50% of the possible values of said first parameter an increase in the value of the first parameter results in an increase in the strength of the alteration.

In some embodiments, the alteration of said pixel is independent of the intensity in the green spectrum relative to the blue spectrum.

According to a third aspect the present disclosure relates to an image processing device for identifying potential pathological vascular structures, said image processing device comprising a processing unit operationally connectable to an image capturing device of a medical device, wherein said processing unit is configured to process an image adapted for computer image analysis using a machine learning data architecture trained to identify potential pathological vascular structures in such images, wherein said image adapted for computer analysis is generated by processing a colour image having a plurality of colour channels recorded by said image capturing device, said colour image has a plurality of pixels wherein the processing of said colour image comprises for at least some of said plurality of pixels the steps of:

(a) process data obtained from a first colour channel together with data obtained from a second colour channel to determine a value of a first parameter indicative of the intensity in the red spectrum relative to the total intensity of said pixel;

(b) using said value of said first parameter to create a pixel value of the image adapted for computer image analysis.

Consequently, by pre-processing the colour images using steps a) and b) the vascular structures may be enhanced making it easier for the machine learning data architecture to identify potential pathological vascular structures. This may both enable the machine learning data architecture to identify more potential pathological vascular structures and perform its processing faster, i.e. using fewer computational resources enabling real time analysis by the machine learning data architecture.

In some embodiments, said machine learning data architecture is a supervised machine learning architecture, trained by being provided with a training data set of images created by steps a) and b), where a first subset of images of said training data set show a pathological vascular structure and a second subset of images of said training data set show a healthy vascular structure.

In some embodiments, the training data set comprises a plurality of images showing vascular structures of tumours.

The plurality of images may be recorded by an image capturing device of a medical device such as an endoscope.

In some embodiments, the pixel values of the image adapted for computer image analysis corresponds to the value of the first parameter optionally multiplied with a weight value derived from said colour image; or the pixel values of the image adapted for computer image analysis is an altered pixel from said colour image altered using the value of said first parameter and wherein the strength of the alteration is dependent on the value of said first parameter.

In some embodiments, said data obtained from the first colour channel is processed together with said data obtained from the second colour channel to create a value of a first sub parameter, said data obtained from said first colour channel is processed together with said data obtained from said third colour channel to create a value of a second sub parameter, and wherein said value of said first sub parameter is processed together with said value of said second sub parameter to create said value of said first parameter.

In some embodiments, said value of said first parameter is created by calculating an average of said value of the first sub parameter and the value of the second sub parameter.

In some embodiments step (a) comprises subtracting said data obtained from the second colour channel from said data obtained from the first colour channel.

In some embodiments, the first parameter may have at least 8 possible values, 16 possible values or 32 possible values.

In some embodiments, both said value of said first sub parameter and said value of said second sub parameter are indicative of the intensity in the red spectrum relative to the total intensity of said pixel.

In some embodiments, said value of said first sub parameter is created by subtracting said data obtained from the second colour channel from said data obtained from the first colour channel, and wherein said value of said second sub parameter is created by subtracting said data obtained from the third colour channel from said data obtained from the first colour channel.

In some embodiments, said processing unit is further configured to: determine a value of a second parameter indicative of the intensity of said pixel and wherein said value of said first parameter together with said value of said second parameter are used to create said pixel value of the image adapted for computer image analysis.

In some embodiments, said plurality of colour channels are normalized prior to being processed together.

In some embodiments, a low pass filtered image is created for each of said plurality of colour channels indicate a local average for each pixel, and wherein each colour channel is normalized using its low pass filtered image.

In some embodiments, said value of said first sub parameter is created by subtracting said data obtained from the second colour channel from said data obtained from the first colour channel, and wherein said value of said second sub parameter is created by subtracting said data obtained from the third colour channel from said data obtained from the first colour channel.

In some embodiments, said colour image is a RGB colour image said first colour channel being the red colour channel and said second colour channel being the green or blue colour channel.

In some embodiments, a high value of the first parameter indicates a high intensity in the red spectrum relative to the total intensity of said pixel and a low value of the first parameter indicates a low intensity in the red spectrum relative to the total intensity of said pixel.

In some embodiments, values of the first parameter that are among the 50% highest of all possible values results in alterations that are more significant than the alterations that results from values of the first parameter that are among the 50% lowest of all possible values.

In some embodiments, for at least 50% of the possible values of said first parameter an increase in the value of the first parameter results in an increase in the strength of the alteration.

In some embodiments, the alteration of said pixel is independent of the intensity in the green spectrum relative to the blue spectrum.

In some embodiments, the machine learning data architecture is an artificial neural network such as a deep structured learning architecture.

In some embodiments, the processing unit is directly operationally connectable to the image capturing device and configured to receive the colour image and perform steps a) and b) to create the image adapted for computer image analysis.

In some embodiments, the processing unit is indirectly operationally connectable to the image capturing device via another image processing device.

In some embodiments, said image processing device is configured to receive said image adapted for computer image analysis from said another image processing device, said another image processing device being configured to receive the colour image and perform steps a) and b) to create the image adapted for computer image analysis.

According to a fourth aspect, the present disclosure relates to a display unit for displaying images obtained by an image capturing device of a medical device, wherein said display unit comprises an image processing device as disclosed in relation to the second aspect of the present disclosure or the third aspect of the present disclosure.

According to a fifth aspect, the present disclosure relates to an endoscope system comprising an endoscope and an image processing device as disclosed in relation to the second aspect of the present disclosure or the third aspect of the present disclosure, wherein said endoscope has an image capturing device and said processing unit of said image processing device is operationally connectable to said image capturing device of said endoscope.

In some embodiments, the endoscope system further comprises a display unit as disclosed in relation to the fourth aspect of the present disclosure, wherein said display unit is operationally connectable to said image capturing device of said endoscope and configured display said captured images.

According to a sixth aspect the present disclosure relates to a computer program product comprising program code means adapted to cause a data processing system to perform the steps of the method disclosed in relation to the first aspect of the present disclosure, when said program code means are executed on the data processing system.

In some embodiments, said computer program product comprises a non-transitory computer-readable medium having stored thereon the program code means.

According to a seventh aspect the present disclosure relates to a data processing system configured to perform the method disclosed in relation to the first aspect of the present disclosure.

The different aspects of the present disclosure can be implemented in different ways including methods, image processing devices, display units, endoscope systems, and compute program products described above and in the following, each yielding one or more of the benefits and advantages described in connection with at least one of the aspects described above, and each having one or more preferred embodiments corresponding to the preferred embodiments described in connection with at least one of the aspects described above and/or disclosed in the dependant claims. Furthermore, it will be appreciated that embodiments described in connection with one of the aspects described herein may equally be applied to the other aspects.

BRIEF DESCRIPTION OF THE DRAWINGS

The above and/or additional objects, features and advantages of the present disclosure, will be further elucidated by the following illustrative and non-limiting detailed description of embodiments of the present disclosure, with reference to the appended drawings, wherein.

DETAILED DESCRIPTION

In the following description, reference is made to the accompanying figures, which show by way of illustration how the embodiments of the present disclosure may be practiced.

Figure 1:
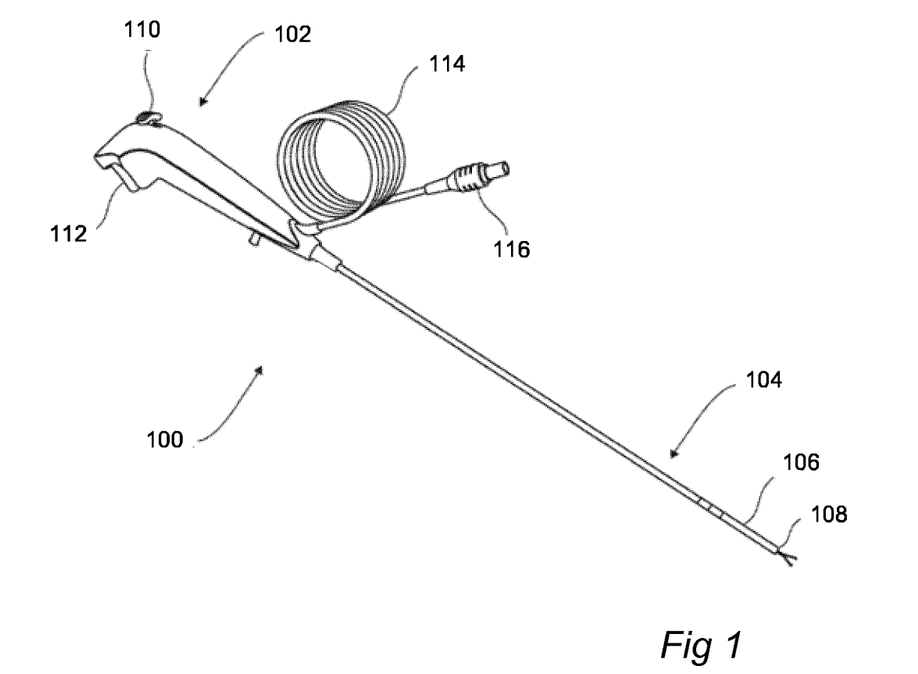
FIG. 1 shows an example of an endoscope.

FIG. 1 illustrates an example of an endoscope 100. This endoscope may be adapted for single-use. The endoscope 100 is provided with a handle 102 attached to an insertion tube 104 provided with a bending section 106. The insertion tube 104 as well as the bending section 106 may be provided with one or several working channels such that instruments, such as a gripping device, may be inserted into a human body via the endoscope. One or several exit holes of the one or several channels may be provided in a tip part 108 of the endoscope 100. In addition to the exit holes, a camera sensor, such as a CMOS sensor or any other image capturing device, as well as one or several light sources, such as light emitting diodes (LEDs), fiber, or any other light emitting devices, may be placed in the tip part 108. By having the camera sensor and the light sources and a monitor 200, illustrated in FIG. 2, configured to display images based on image data captured by the camera sensor, an operator is able to see and analyze an inside of the human body in order to for instance localize a position for taking a sample. In addition, the operator will be able to control the instrument in a precise manner due to the visual feedback made available by the camera sensor and the monitor. Further, since some diseases or health issues may result in a shift in natural colors or other visual symptoms, the operator is provided with valuable input for making a diagnosis based on the image data provided via the camera sensor and the monitor.

In order to make it possible for the operator to direct the camera sensor such that different field of views can be achieved, the endoscope has a bending section 106 that can be bent in different directions with respect to the insertion tube 104. The bending section 106 may be controlled by the operator by using a knob 110 placed on the handle 102. The handle 102 illustrated in FIG. 1 is designed such that the knob 110 is controlled by a thumb of the operator, but other designs are also possible. In order to control a gripping device or other device provided via a working channel a push button 112 may be used. The handle 102 illustrated in FIG. 1 is designed such that a pointer finger of the operator is used for controlling the gripping device, but other designs are also possible.

Figure 2:
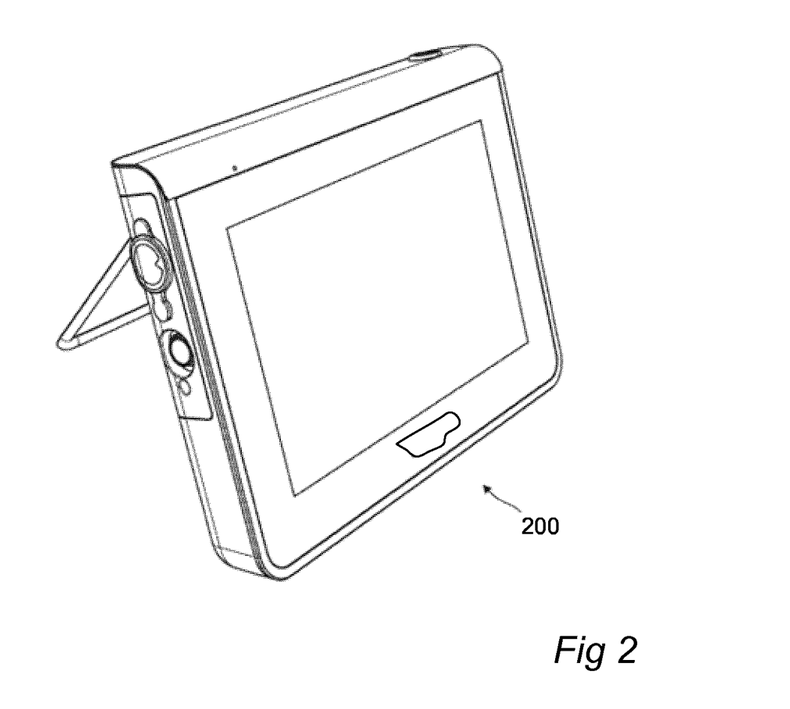
FIG. 2 shows an example of a display unit that can be connected to the endoscope shown in FIG. 1.

The image data captured by the camera sensor and optionally also other data captured by other sensors placed in the tip part can be transferred via a connection cable 114 and a connector 116 to a display unit 200 illustrated in FIG. 2. Even though wire-based data transmission is illustrated, it is equally possible to transfer image data by using wireless data transmission.

The display unit 200 is preferably a re-usable piece of equipment. By having one single-use piece of equipment and another re-usable piece of equipment, most of the data processing capability may be placed in the re-usable piece of equipment in order to reach a cost efficient level at the same time as being safe to use from a health perspective.

The display unit 200 may comprise an image processing device as explained in relation to the second aspect of the disclosure and/or the third aspect of the disclosure.

Figure 3:
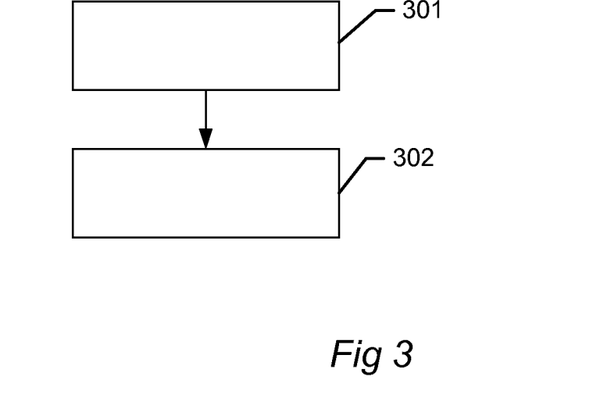
FIG. 3 shows a flow chart of a method of enhancing the visibility of blood vessels in a colour image captured by an image capturing device of a medical device according to an embodiment of the disclosure.

FIG. 3 shows a flowchart of a method of enhancing the visibility of blood vessels in a colour image according to an embodiment of the disclosure. The colour image has a plurality of colour channels and a plurality of pixels, wherein the method comprises for at least some of the plurality of pixels the steps of: 301 processing data obtained from a first colour channel together with data obtained from a second colour channel to determine a value of a first parameter indicative of the intensity in the red spectrum relative to the total intensity of the pixel; 302 using the value of the first parameter to alter the pixel, wherein the first parameter has at least three possible values, and wherein the strength of the alteration is dependent on the value of the first parameter.

Figure 4:
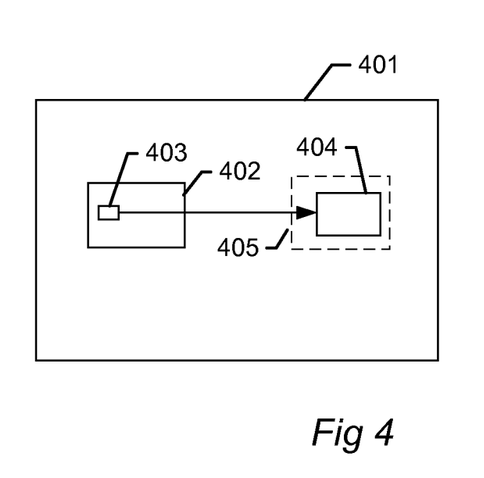
FIG. 4 shows a schematic drawing of an endoscope system according to an embodiment of the present disclosure.

FIG. 4 shows a schematic drawing of an endoscope system 401 according to an embodiment of the disclosure. The endoscope system 401 comprises an endoscope 402 and an image processing device 404 as disclosed in relation to the second aspect of the disclosure and/or the third aspect of the disclosure, wherein the endoscope 402 has an image capturing device 403 and the processing unit of the image processing device 404 is operationally connectable to the image capturing device of the endoscope 403. In this embodiment, the image processing device 404 is integrated in a display unit 405 configured to display the enhanced captured images.

Figure 5:
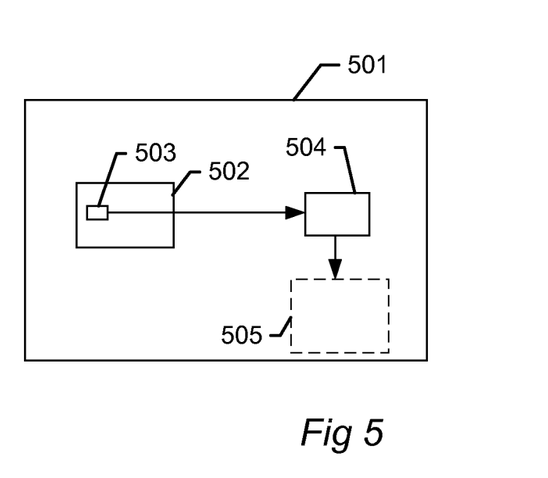
FIG. 5 shows a schematic drawing of an endoscope system according to an embodiment of the present disclosure.

FIG. 5 shows a schematic drawing of an endoscope system 501 according to an embodiment of the disclosure. The endoscope system 501 comprises an endoscope 502 and an image processing device 504 as disclosed in relation to the second aspect of the disclosure and/or the third aspect of the disclosure, wherein the endoscope 502 has an image capturing device 503 and the processing unit of the image processing device 504 is operationally connectable to the image capturing device of the endoscope 503. In this embodiment, the image processing device 504 is provided as an independent unit operationally connectable to a display unit 505 configured to display the enhanced captured images.

Figure 6:
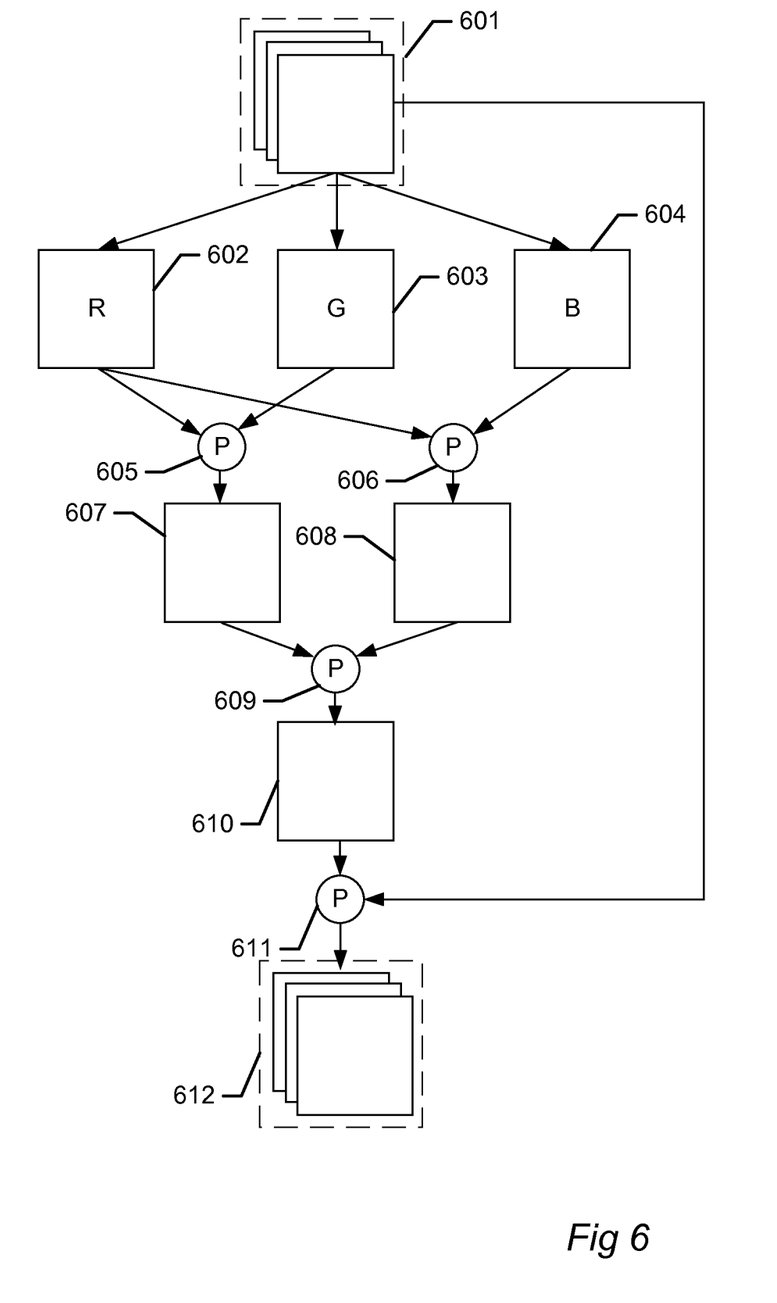
FIG. 6 shows a flow chart of a method of enhancing the visibility of blood vessels in a colour image captured by an image capturing device of a medical device according to an embodiment of the disclosure.

FIG. 6 shows a flowchart of a method of enhancing the visibility of blood vessels in a colour image captured by an image capturing device of a medical device. Shown is a single colour image 601 having a plurality of colour channels. In this embodiment the colour image 601 is coded in a RGB colour space. In the first step, the colour image 601 is split in the red colour channel 602, the green colour channel 603, and the blue colour channel 604. Next for each pixel, a value of a first sub parameter is created by subtracting 605 data obtained from the green colour channel 603 (e.g. the green intensity value) from data obtained from the red colour channel 602 (e.g. the red intensity value). This results in a first sub parameter image 607. Correspondingly, for each pixel, a value of a second sub parameter is created by subtracting 606 data obtained from the blue colour channel 604 (e.g. the blue intensity value) from data obtained from the red colour channel 602 (e.g. the red intensity value). This results in a second sub parameter image 608. Then, for each pixel, a value of a first parameter is created by calculating an average 609 of the value of the first sub parameter and the value of the second sub parameter. This results in a first parameter image 610. The first parameter has at least three possible values e.g. at least 8, 16, 32, 64, 128, 256 possible values. The first parameter image 610 shows regions in the colour image 601 where the intensity in the red spectrum relative to the total intensity is high. This has shown to be a reliable indicator of blood vessels. Finally, the first parameter image 610 is used to alter 611 the original colour image 601 creating an altered image 612, wherein the strength of the alteration is dependent on the value of the first parameter. As an example, for each pixel, the value of the first parameter may be subtracted from the value of each colour channel in the colour image 601. This will have the effect that the blood vessels will become darker and the remaining parts of the image will become brighter. However, the colours will be left substantially unaffected. The overall intensity of the altered image 612 may subsequently be lowered so that the intensity of the areas of the altered image 612 without blood vessels will have an intensity substantially matching the intensity of the corresponding areas in the original colour image 601.

Figure 7:
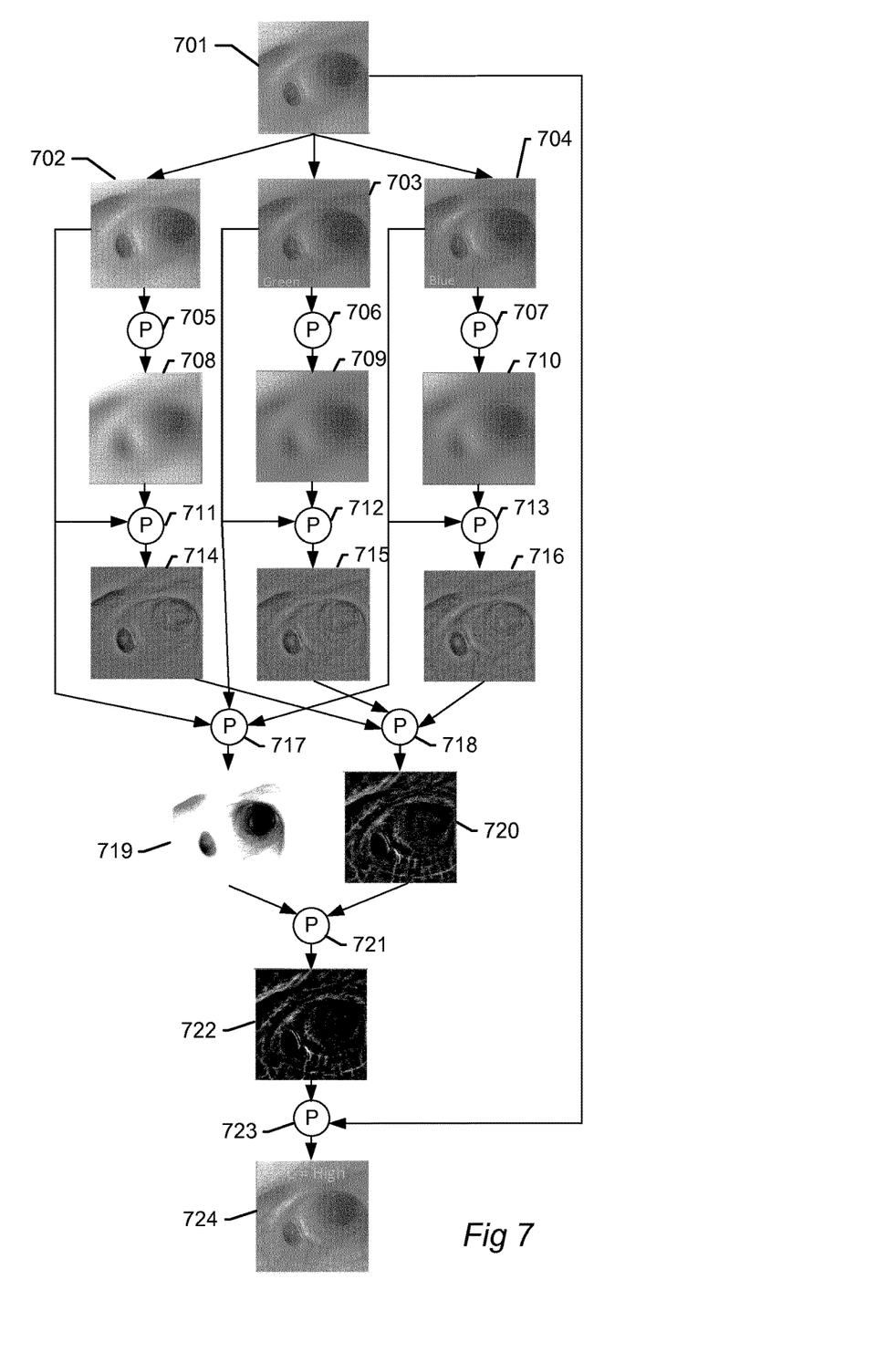
FIG. 7 shows a flow chart of a method of enhancing the visibility of blood vessels in a colour image captured by an image capturing device of a medical device according to an embodiment of the disclosure.

FIG. 7 shows a flowchart of a method of enhancing the visibility of blood vessels in a colour image captured by an image capturing device of a medical device. Shown is a single colour image 701 having a plurality of colour channels. In this embodiment the colour image 701 is coded in a RGB colour space. In the first step, the colour image 701 is split in the red colour channel 702, the green colour channel 703, and the blue colour channel 704. Next, the red colour channel 702 is low pass filtered 705 creating a low pass filtered red colour channel 708, the green colour channel 703 is low pass filtered 706 creating a low pass filtered green colour channel 709, and the blue colour channel is low pass filtered 707 creating a low pass filtered blue colour channel 710. The low pass filtered colour channels 708-710 show local averages for each pixel. Next, the low pass filtered red colour channel 708 is used to normalize 711 the red colour channel 702 creating a normalized red colour channel 714, the low pass filtered green colour channel 709 is used to normalize 712 the green colour channel 703 creating a normalized green colour channel 715, and the low pass filtered blue colour channel 710 is used to normalize 714 the blue colour channel 704 creating a normalized blue colour channel 716. Then, the normalized colour channels 714-716 are processed together 718 to create a first parameter image 720 indicative of the intensity in the red spectrum relative to the total intensity. The normalized colour channels 714-716 may be processed together 718 to create the first parameter image 720 in the same way as the colour channels 602-604 in FIG. 6 are processed together to create the first parameter image 610. Next, the red, green, and blue colour channel 702-704 are processed together to determining a value of a second parameter indicative of the intensity of each pixel e.g. by summing the red, green, and blue colour channel 702-704, creating a second parameter image 719. Next, the first parameter image 720 and the second parameter image 719 are processed together 721 to create an alteration parameter image 722. This may be done by per pixel multiplying the first parameter image 720 with the second parameter image 719. Finally, the alteration parameter image 722 is used to alter 723 the original colour image 701 creating an altered image 724, wherein the strength of the alteration is dependent on the value of the alteration parameter image 722.

Figure 8A:
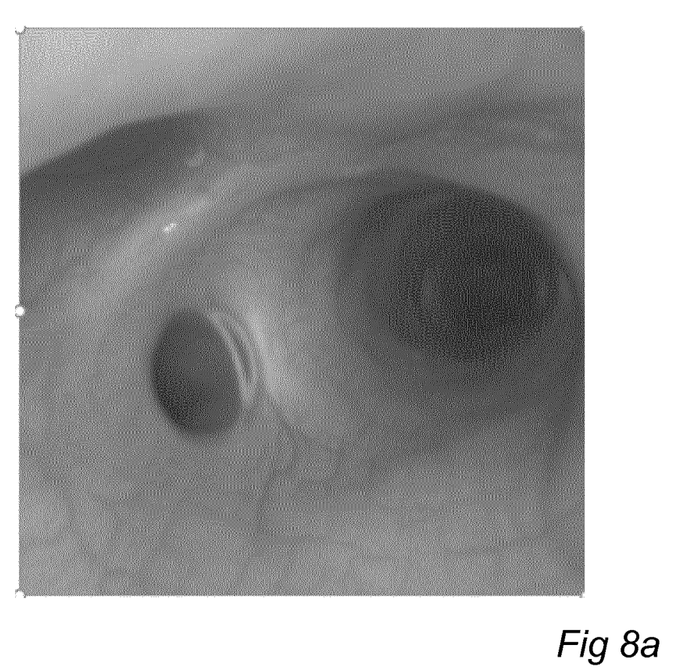
FIG. 8a shows a colour image of an internal cavity before the visibility of the blood vessels have been enhanced and FIG. 8b shows the colour image after the visibility of the blood vessels have been enhanced according to an embodiment of the disclosure.
Figure 8B:
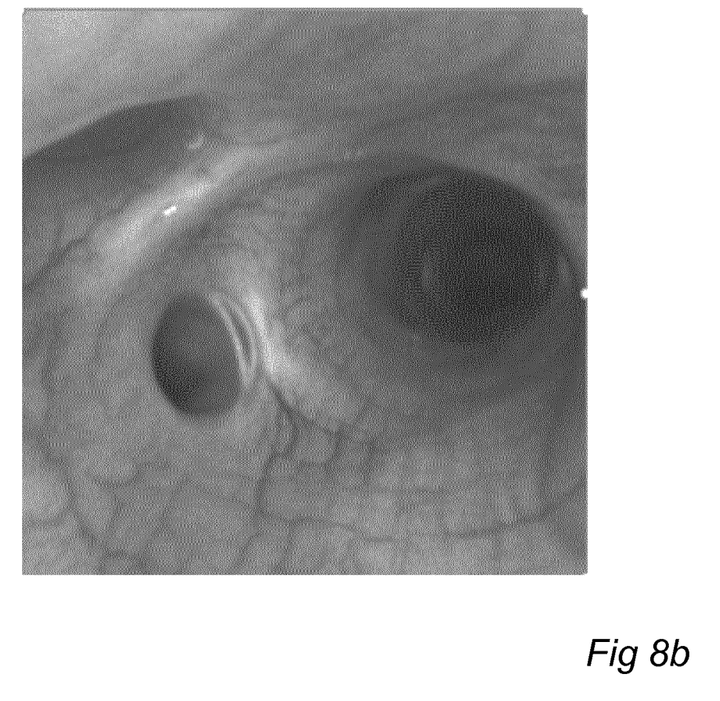

FIG. 8a shows a colour image of an internal cavity before the visibility of the blood vessels have been enhanced and FIG. 8b shows the colour image after the visibility of the blood vessels have been enhanced according to an embodiment of the disclosure. It can be seen that the blood vessels are more clear in the image in FIG. 8b while the presentation of the other tissue types are substantially unchanged. This will allow the medical personal to effectively examine both the vascular structures and the other areas of the internal cavity for pathological changes.

Figure 9:
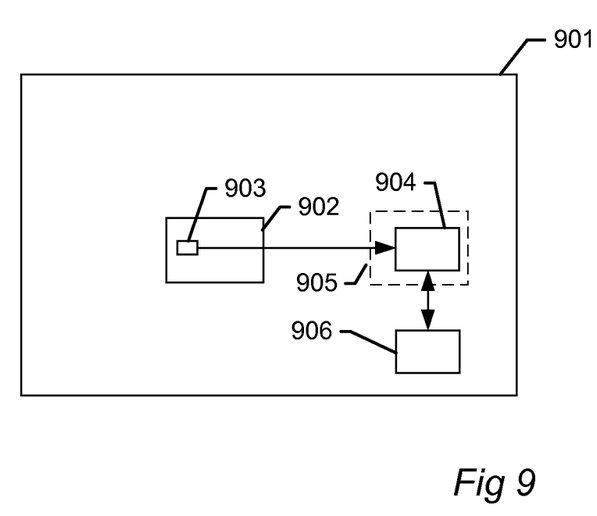
FIG. 9 shows a schematic drawing of an endoscope system 901 according to an embodiment of the disclosure.

FIG. 9 shows a schematic drawing of an endoscope system 901 according to an embodiment of the disclosure. The endoscope system 901 comprises an endoscope 902, a first image processing device 904, and a second image processing device 906, where both the first image processing device 904 and the second image processing device 906 have a processing unit. The endoscope 902 has an image capturing device 903 and the processing unit of the first image processing device 904 is operationally connectable to the image capturing device of the endoscope 903. In this embodiment, the first image processing device 904 is integrated in a display unit 905 and the processing unit of the second image processing device 906 is directly operationally connectable to the processing unit of the first image processing device 904 and indirectly operationally connectable to the image capturing device of the endoscope 903 via the first image processing device 904. In this embodiment the processing unit of the first image processing device 904 is configure to generate an image adapted for computer image analysis by processing a colour image having a plurality of colour channels recorded by the image capturing device 903, the colour image has a plurality of pixels wherein the processing of the colour image comprises for at least some of said plurality of pixels the steps of:

(a) process data obtained from a first colour channel together with data obtained from a second colour channel to determine a value of a first parameter indicative of the intensity in the red spectrum relative to the total intensity of said pixel;

(b) using said value of said first parameter to create a pixel value of the image adapted for computer image analysis. The image adapted for computer image analysis is forward to the second image processing device 906 where the image adapted for computer analysis is processed using a machine learning data architecture trained to identify potential pathological vascular structures in such images. The second image processing unit 906 may be arranged in proximity of the first image processing device 904, where the first and second image processing device 904 906 communicate directly or via a local network. Alternatively, the second image processing device may be arranged remotely from the first image processing device and communicate via WAN such as the internet. The output from the machine learning data architecture may be a notification provided to the first image processing device 904. The notification may simply specify that a potential pathological vascular structure has been identified. However, the notification may also indicate the type of pathology and/or the location in the image. If the notification specifies the location of the potential pathology, then the display unit 905 may be configured to highlight the part of the image where the potential pathology has been identified. The image adapted for computer analysis may more clearly show the vascular structures (compared to the original colour image) thereby making it easier for the machine learning data architecture to identify potential pathological vascular structures. Examples of images adapted for computer analysis are (with reference to the FIG. 7 embodiment) the altered image 724, the first parameter image 720, and the alteration parameter image 722.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:

1. A method of operating an image processing device for enhancing the visibility of blood vessels in a colour image captured by an image capturing device of a medical device, said colour image having a plurality of colour channels including a red colour channel, a green colour channel, and a blue colour channel and having a plurality of pixels, wherein said method comprises, for at least some of said plurality of pixels, the steps of:

(a) processing data obtained from the red colour channel together with data obtained from the green colour channel to create a value of a first sub parameter, and processing data obtained from the red colour channel together with data obtained from the blue colour channel to create a value of a second sub parameter, wherein said processing comprises subtracting said data obtained from the green colour channel from said data obtained from the red colour channel;

processing said value of said first sub parameter together with said value of said second sub parameter to create a value of a first parameter indicative of the intensity in a red spectrum relative to a total intensity of said pixel; and (b) using said value of said first parameter to alter said pixel, wherein said first parameter has at least three possible values, and wherein the strength of the alteration is dependent on the value of said first parameter.

2. The method according to claim 1, wherein step (a) comprises: processing data obtained from the blue colour channel to determine the value of said first parameter.

3. The method according to claim 1, wherein both said value of said first sub parameter and said value of said second sub parameter are indicative of the intensity in the red spectrum relative to the total intensity of said pixel.

4. The method according to claim 1, wherein parts of the colour image having no blood vessels are substantially unaltered and displayed with normal colours.

5. The method according to claim 1, wherein said method further comprises:

determining a value of a second parameter indicative of the intensity of said pixel and wherein said value of said first parameter together with said value of said second parameter are used to alter said pixel.

6. The method according to claim 1, wherein said plurality of colour channels are normalized prior to being processed together.

7. The method according to claim 6, wherein a low pass filtered image is created for each of said plurality of colour channels indicating a local average for each pixel, and wherein each colour channel is normalized using its low pass filtered image.

8. The method according to claim 7, wherein a value of a third parameter is created based on user input, and wherein the alteration is dependent on both said value of said first parameter and said value of said third parameter, whereby the user may control the strength of the alteration.

9. The method according to claim 1, wherein a high value of the first parameter indicates a high intensity in the red spectrum relative to the total intensity of said pixel and a low value of the first parameter indicates a low intensity in the red spectrum relative to the total intensity of said pixel, wherein values of the first parameter that are among the 50% highest of all possible values results in alterations that are more significant than the alterations that result from values of the first parameter that are among the 50% lowest of all possible values.

10. The method according to claim 9, wherein for at least 50% of the possible values of said first parameter an increase in the value of the first parameter results in an increase in the strength of the alteration.

11. An image processing device for enhancing the visibility of blood vessels in a colour image, said image processing device comprising a processing unit operationally connectable to an image capturing device of a medical device, wherein said processing unit is configured to receive a colour image having a plurality of colour channels including a red colour channel, a green colour channel, and a blue colour channel from said image capturing device, said colour image has a plurality of pixels and said processing unit further is configured to, for at least some of said plurality of pixels, perform the steps of:
(a) process data obtained from the red colour channel together with data obtained from the green colour channel to create a value of a first sub parameter, and process data obtained from the red colour channel together with data obtained from the blue colour channel to create a value of a second sub parameter, wherein said process data comprises subtracting said data obtained from the green colour channel from said data obtained from the red colour channel;
process said value of said first sub parameter together with said value of said second sub parameter to create a value of a first parameter indicative of the intensity in a red spectrum relative to a total intensity of said pixel; and
(b) using said value of said first parameter to alter said pixel,
wherein said first parameter has at least three possible values, and wherein the strength of the alteration is dependent on the value of said first parameter.

12. The image processing device according to claim 11, wherein step (a) comprises: processing data obtained from the blue colour channel to determine the value of said first parameter.

13. The image processing device according to claim 11, wherein both said value of said first sub parameter and said value of said second sub parameter are indicative of the intensity in the red spectrum relative to the total intensity of said pixel.

14. The image processing device according to claim 11, wherein parts of the colour image having no blood vessels are substantially unaltered and displayed with normal colours.

15. The image processing device according to claim 11, wherein said image processing device is operationally connectable to an input unit for receiving user input and further configured to receive a user selected value of a third parameter from said input unit and wherein the alteration is dependent on both said value of said first parameter and said value of said third parameter, whereby the user may control the strength of the alteration.

16. A display unit for displaying images obtained by an image capturing device of a medical device, wherein said display unit comprises:
the image processing device according to claim 11.

17. An endoscope system comprising:
an endoscope; and
the image processing device according to claim 11,
wherein said endoscope has an image capturing device and said processing unit of said image processing device is operationally connectable to said image capturing device of said endoscope.

18. The endoscope system according to claim 17, wherein the endoscope system further comprises a display unit, wherein said display unit is operationally connectable to said image capturing device of said endoscope and configured display said captured images.

19. A method of operating an image processing device for enhancing the visibility of blood vessels in a colour image captured by an image capturing device of a medical device, said colour image having a plurality of colour channels including a red colour channel, a green colour channel, and a blue colour channel and having a plurality of pixels, wherein said method comprises, for at least some of said plurality of pixels, the steps of:
(a) processing data obtained from the red colour channel together with data obtained from the green colour channel to create a value of a first sub parameter, and processing data obtained from the red colour channel together with data obtained from the blue colour channel to create a value of a second sub parameter;
processing said value of said first sub parameter together with said value of said second sub parameter to create a value of a first parameter indicative of the intensity in a red spectrum relative to a total intensity of said pixel; and
(b) using said value of said first parameter to alter said pixel,
wherein said first parameter has at least three possible values, and wherein the strength of the alteration is dependent on the value of said first parameter, and
wherein prior to step (a):
a low pass filtered image is created for each of said plurality of colour channels indicating a local average for each pixel, and each colour channel of said plurality of colour channels is normalized using its low pass filtered image.

20. The method according to claim 19, wherein step (a) comprises: processing data obtained from the blue colour channel to determine the value of said first parameter.

21. The method according to claim 19, wherein step (a) comprises subtracting said data obtained from the green colour channel from said data obtained from the red colour channel.

22. The method according to claim 19, wherein said method further comprises:
determining a value of a second parameter indicative of the intensity of said pixel and wherein said value of said first parameter together with said value of said second parameter are used to alter said pixel.

23. The method according to claim 19, wherein a value of a third parameter is created based on user input, and wherein the alteration is dependent on both said value of said first parameter and said value of said third parameter, whereby the user may control the strength of the alteration.

24. The method according to claim 19, wherein a high value of the first parameter indicates a high intensity in the red spectrum relative to the total intensity of said pixel and a low value of the first parameter indicates a low intensity in the red spectrum relative to the total intensity of said pixel, wherein values of the first parameter that are among the 50% highest of all possible values results in alterations that are more significant than the alterations that result from values of the first parameter that are among the 50% lowest of all possible values.

25. A method of operating an image processing device for enhancing the visibility of blood vessels in a colour image captured by an image capturing device of a medical device, said colour image having a plurality of colour channels including a red colour channel, a green colour channel, and a blue colour channel and having a plurality of pixels, wherein said method comprises, for at least some of said plurality of pixels, the steps of:
(a) processing data obtained from the red colour channel together with data obtained from the green colour channel to create a value of a first sub parameter, and processing data obtained from the red colour channel together with data obtained from the blue colour channel to create a value of a second sub parameter;
processing said value of said first sub parameter together with said value of said second sub parameter to create a value of a first parameter indicative of the intensity in a red spectrum relative to a total intensity of said pixel; and
(b) using said value of said first parameter to alter said pixel,
wherein said first parameter has at least three possible values, and wherein the strength of the alteration is dependent on the value of said first parameter, and
wherein a high value of the first parameter indicates a high intensity in the red spectrum relative to the total intensity of said pixel and a low value of the first parameter indicates a low intensity in the red spectrum relative to the total intensity of said pixel, wherein values of the first parameter that are among the 50% highest of all possible values results in alterations that are more significant than the alterations that result from values of the first parameter that are among the 50% lowest of all possible values.

26. The method according to claim 25, wherein step (a) comprises: processing data obtained from the blue colour channel to determine the value of said first parameter.

27. The method according to claim 25, wherein step (a) comprises subtracting said data obtained from the green colour channel from said data obtained from the red colour channel.

28. The method according to claim 25, wherein said method further comprises:
determining a value of a second parameter indicative of the intensity of said pixel and wherein said value of said first parameter together with said value of said second parameter are used to alter said pixel.

29. The method according to claim 25, wherein a low pass filtered image is created for each of said plurality of colour channels indicating a local average for each pixel, and wherein each colour channel is normalized using its low pass filtered image.

30. The method according to claim 25, wherein a value of a third parameter is created based on user input, and wherein the alteration is dependent on both said value of said first parameter and said value of said third parameter, whereby the user may control the strength of the alteration.

31. An image processing device for enhancing the visibility of blood vessels in a colour image, said image processing device comprising a processing unit operationally connectable to an image capturing device of a medical device, wherein said processing unit is configured to receive a colour image having a plurality of colour channels including a red colour channel, a green colour channel, and a blue colour channel from said image capturing device, said colour image has a plurality of pixels and said processing unit further is configured to, for at least some of said plurality of pixels, perform the steps of:
(a) process data obtained from the red colour channel together with data obtained from the green colour channel to create a value of a first sub parameter, process data obtained from the red colour channel together with data obtained from the blue colour channel to create a value of a second sub parameter;
process said value of said first sub parameter together with said value of said second sub parameter to create a value of a first parameter indicative of the intensity in a red spectrum relative to a total intensity of said pixel;
(b) using said value of said first parameter to alter said pixel,
wherein said first parameter has at least three possible values, and wherein the strength of the alteration is dependent on the value of said first parameter,
wherein said image processing device is operable to receive a user selected value of a third parameter, and wherein the alteration is dependent on both said value of said first parameter and said value of said third parameter, whereby the user may control the strength of the alteration with the user selected value.

32. The image processing device according to claim 31, wherein step (a) comprises: processing data obtained from the blue colour channel to determine the value of said first parameter.

33. The image processing device according to claim 31, wherein both said value of said first sub parameter and said value of said second sub parameter are indicative of the intensity in the red spectrum relative to the total intensity of said pixel.

34. The image processing device according to claim 31, wherein step (a) comprises subtracting said data obtained from the green colour channel from said data obtained from the red colour channel.

* * * * *